United States Patent [19]

Cliffton et al.

[11] Patent Number: 4,851,589
[45] Date of Patent: Jul. 25, 1989

[54] OXIDATIVE COUPLING OF ALKYLPHENOLS BY COPPER CATALYSTS

[75] Inventors: Michael D. Cliffton, Martinez; Stephen J. Carter, Augusta, both of Ga.

[73] Assignee: Amoco Corporation

[21] Appl. No.: 98,814

[22] Filed: Sep. 18, 1987

[51] Int. Cl.$^4$ .............................................. C07C 39/12
[52] U.S. Cl. .................................................. 568/730
[58] Field of Search ................................ 568/722, 730

[56] References Cited

U.S. PATENT DOCUMENTS

| | | | |
|---|---|---|---|
| 3,210,384 | 10/1965 | Hay et al. | 556/110 |
| 3,247,262 | 4/1966 | Kaeding | 568/730 |
| 3,306,874 | 2/1967 | Hay | 568/730 |
| 3,306,875 | 2/1967 | Hay | 568/730 |
| 3,631,208 | 12/1971 | Hay | 568/730 |
| 3,812,193 | 5/1974 | Randell et al. | 568/730 |
| 3,914,266 | 10/1975 | Hay | 556/110 |
| 4,070,383 | 1/1978 | Rutledge | 568/730 |
| 4,085,124 | 4/1978 | Rutledge | 568/730 |
| 4,100,202 | 7/1978 | Rutledge | 568/730 |
| 4,180,686 | 12/1979 | Dodd | 568/730 |
| 4,195,189 | 3/1980 | Earley | 568/730 |
| 4,594,405 | 6/1986 | Haltko | 556/110 |
| 4,595,773 | 6/1986 | White | 556/110 |

*Primary Examiner*—Werren B. Lone

[57] ABSTRACT

This invention relates to the use of copper catalysts in the oxidative coupling of 2,6-dialkylphenols to produce mixtures of 3,3′,5,5′-tetra-alkyl-4,4′-dihydroxybiphenyls and corresponding diphenoquinones.

12 Claims, No Drawings

OXIDATIVE COUPLING OF ALKYLPHENOLS BY COPPER CATALYSTS

BACKGROUND OF THE INVENTION

This invention relates to the use of copper catalysts in the oxidative coupling of 2,6-dialkylphenols. More specifically, this invention relates to copper amine salt complexes having high catalytic activity in the coupling of 2,6-dialkylphenols to produce mixtures of 3,3', 5,5'-tetra-alkyl-4,4'-dihydroxybiphenyls (also known as 3,3', 5,5'-tetra-alkylbiphenols) and corresponding diphenoquinones.

The prior art discloses that 3,3', 5,5'-tetra-alkylbiphenols, which are important precursors in the synthesis of 4,4'-biphenol, were prepared either from 3,3', 5,5'-tetra-alkyl-4,4'-diphenoquinones or by direct conversion of 2,6-dialkylphenols. The oxidative coupling reaction which produces diphenoquinone structures has, in most instances, been accomplished in the presence of an organometallic complex which acts as a catalyst. The use of a catalyst allows the reaction to be carried out at lower temperatures under milder conditions.

The concentration of the catalyst is an important consideration in this process. In general, the use of high catalyst concentrations results in shorter reaction times, but this is counter balanced by high levels of catalyst residuals in the product, which require elaborate purification measures for removal. Therefore, the oxidative coupling of 2,6-dialkylphenols with a minimum quantity of catalyst is highly desirable to maintain reaction times of reasonable duration.

Formation of tetra-alkylbiphenols via diphenoquinones can be accomplished either by (a) standard quinone reduction techniques, which reduces product yield, or (b) through a disproportionation reaction in which the diphenoquinone reacts with two molar equivalents of the appropriate 2,6-dialkylphenol to give two molar equivalents of the tetra-alkylbiphenol. The disproportionation reaction is further described in U.S. Pat. No. 3,631,208.

An improvement on this technology involves eliminating the disproportionation step by directly converting 2,6-dialkylphenols to 3,3', 5,5'-tetra-alkylbiphenols during the oxidation step as illustrated below:

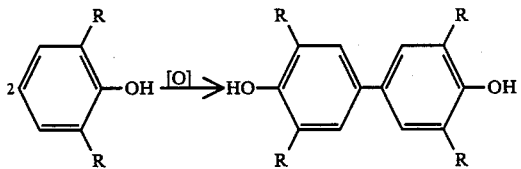

One stage processes for this oxidation are disclosed in the following U.S. patents, but all of these methods necessitate stringent reaction conditions, difficult product work-up procedures and high concentrations of catalyst.

U.S. Pat. No. 3,812,193 discloses the oxidation of 2,6-diisopropylphenol to the corresponding biphenol using a ferric aqueous medium. These processes incorporate product isolation procedures which are exceedingly difficult to scale-up to a commercial level.

A one-step procedure to alkylated biphenols is described in U.S. Pat. No. 4,180,686. Palladium acetate was found to catalyze the oxidation of di- and trialkylated phenols to corresponding alkylated biphenols in polar organic solvents. The major disadvantages with this process are the requirements for high oxygen pressure (50–100 psig) and the positions of phenol ring functionality. In order to avoid large amounts of diphenoquinone formation, at least one alkyl group must be meta to the phenol function. This process is also complicated by the use of organic solvents which must be removed in work-up.

U.S. Pat. No. 3,247,262 demonstrates the oxidation of 2,6-dialkylphenols to the tetra-alkylated biphenol without a solvent. The reaction was performed in the presence of stoichiometric quantities of a cupric carboxylate salt at rather high reaction temperatures of 140°–255° C.

U.S. Pat. No. 4,195,189 discloses a similar type of oxidation which utilizes an activated basic cupric oxide having a surface area of approximately 5–50 square meters/gram. This process has the disadvantage of requiring a 1.0 to 1.8 ratio of cupric oxide to 2,6-dialkylphenol. The product, therefore, must be leached away from the cupric oxide with a polar organic solvent or a halogenated hydrocarbon, thus complicating the process.

BRIEF SUMMARY OF THE INVENTION

We have discovered that carbon-carbon coupled condensation products can be effectively prepared from a 2,6-dialkylphenol by reacting the 2,6-dialkylphenol in the presence of oxygen, a copper amine salt complex catalyst and an acidic phenol. The catalyst can be made in a variety of solvents including the 2,6-dialkylphenol to be oxidized.

The copper amine salt complexes of this invention exhibit improved catalyst activity from similar systems described in U.S. Pat. Nos. 3,306,874 and 3,306,875. The key to this improved catalyst activity is related to the use of an acidic phenol in the coupling reaction. This will be discussed in detail later in our disclosure.

The oxidation reaction of this invention can be performed in the 2,6-dialkylphenol selected for coupling without any other solvent.

DETAILED DESCRIPTION OF INVENTION

Catalyst Preparation

The catalysts utilized in our invention are made by reacting a copper halide with tetra-methylethylenediamine (TMEDA). In this application, the term "copper halide" will be understood to include cuprous chloride, cuprous bromide, cupric chloride and cupric bromide. The preferred copper halide is cuprous chloride. Although useful, the catalysts made from cupric chloride or cupric bromide are less active than the cuprous-based catalysts.

The copper amine salt complex can be made in low molecular weight alcohols, halogenated hydrocarbons, or the 2,6-dialkylphenol to be oxidatively coupled.

Examples of suitable low molecular weight alcohols are methanol, ethanol and 2-propanol. Examples of suitable halogenated hydrocarbons are dichloromethane, 1,1'-dichloroethane and 1,2-dichloroethane.

In preparing the catalyst complex, the preferred medium is the 2,6-dialkylphenol to be oxidized.

Formation of the catalyst complex should be accomplished in the absence of oxygen. In this case, the oxidation can be performed without catalyst solution transfer. However, we prefer that the catalyst be made in the 2,6-dialkylphenol in a concentrated solution and then transferred to the main body of 2,6-dialkylphenol before coupling in the presence of oxygen. This shortens the time required to complete the copper amine salt complex formation.

When catalyst formation is performed in alcohols or halogenated hydrocarbons, the catalyst solution is added to the main body of the 2,6-dialkylphenol, and the solvent is then removed by distillation prior to oxidation.

In a preferred embodiment of this invention, the catalyst is prepared by first suspending a cuprous halide in the 2,6-dialkylphenol at 35°–50° C. Then TMEDA is added with stirring in a non-oxygen containing atmosphere. Soluble catalyst is produced within 1–15 minutes of TMEDA addition (depending on the scale of reaction). A critical limitation is that the 2,6-dialkylphenol used in catalyst formation contains no greater than 400 ppm of water. Higher water content results in a catalyst having reduced activity. However, once the copper catalyst has been transformed to the cupric state, the presence of water in the 2,6-dialkylphenol does not significantly reduce the catalytic activity of the complex.

Water can be used as a means of controlling the reaction temperature and should be added to the reaction mixture after the catalyst has been activated. This is preferentially achieved by sparging the catalyst solution with oxygen or air for 1–4 min. Sufficient oxygen should be used to convert 60–100% of the catalyst to the cupric state. Excess oxygen should be avoided as this causes extensive diphenoquinone formation to take place. The latter is especially important at low temperatures where the diphenoquinone might precipitate out, entrapping some of the catalyst. The preferred temperature range is 60°–80°.

If there is no need for water addition, catalyst activation by oxygen is not a prerequisite, although pre-activation may improve the initial rate of the reaction.

The catalyst/2,6-dialkylphenol solution made in the absence of oxygen is for the most part colorless. Adding trace amounts of oxygen to the catalyst solution results in a green colored solution below a temperature of 55° C., transforming to a light brown color above 60°–65° C.

The catalyst complex made in alcohols or halogenated hydrocarbons is a colorless solution which turns blue on exposure to small amounts of oxygen.

The catalyst complex can be made in molar ratios of TMEDA to copper halide varying from 1:0.5 to 5.0. The preferred range for TMEDA: copper halide is 1:1.3. The most preferred embodiment of this invention is a ratio of 2.0.

Preferred copper halides which can be used in this invention are cuprous chloride and cuprous bromide.

The concentration range in which the catalyst can be utilized, based on copper in the catalyst solution, is 0.01 to 0.1M. The preferred molarity range is 0.03 to 0.08.

The range of molarity of the copper catalyst, based on copper, in the total 2,6-dialkylphenol body can vary from .002 to 0.4. The preferred molarity range is 0.002 to 0.006.

The molar ratio of catalyst complex to 2,6-dialkylphenol in the reaction mixture should, therefore, be in the range 500–2000: 1, the ideal ration being about 1000:1.

The 2,6-dialkylphenols which are useful in our invention are represented by the formula:

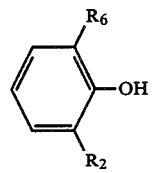

where $R_2$ and $R_6$ are alkyl groups having 3–6 carbons.

Process Conditions

When the catalyst solution is added to the main body of the 2,6-dialkylphenol, preferably the catalyst is prepared in the 2,6-dialkylphenol to be coupled. This avoids having to remove solvent by distillation before starting the oxidation process. However, catalyst solvents (such as methanol or halogenated hydrocarbons) can be distilled from the main body of the dialkylphenol following the charging of the catalyst solution without adversely affecting the oxidation.

The reaction is conducted within a temperature range of 70° to 120° C., but preferably at about 90°–120° C. Oxygen can be admitted to the system by sparging with a tube set below the surface of the liquid at a rate of 1–3 liter/minute or by an inlet into a sealed reactor. The latter method requires sufficient agitation to maintain good oxygen uptake and reasonable reaction times.

The reaction pressure can vary from atmospheric pressure to 20 psig. Preferably, the partial pressure of oxygen is maintained from 70–140 mm Hg. The reaction time suitable for this reaction pressure range is about one to ten hours, preferably 1–3 hours.

This reaction time is sufficient to convert approximately 20–60% of the starting 2,6-dialkylphenol (depending on temperature) to the corresponding 3,3', 5,5'-tetra-alkylbiphenol and diphenoquinone in ratios varying from 30:70 percent to 60:40 percent, depending on the temperature.

Higher process temperatures increase the proportion of tetra-alkylated biphenol, especially in the range 120°–140° where the biphenol becomes the major reaction product.

For a given time period, we have also found that the yield of the coupled phenol products can be increased by some 20–40% through the addition of a small amount of an acidic phenol to the 2,6-dialkylphenol which comprises the main charge of the reaction or which is used to prepare the catalyst, or both. A combination of acidic phenols can be used.

An acidic phenol is defined as any phenol which will react readily with an aqueous solution of an alkali metal hydroxide at ambient temperture to form a salt plus water. Preferred examples of such phenols include phenol; 2-t-butylphenol (2-TBP) and m-cresol.

The acidic phenols useful in this invention have the structural formula:

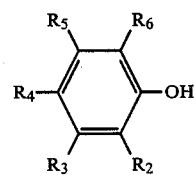

wherein each $R_2$, $R_3$, $R_4$, $R_5$ and $R_6$ is independently hydrogen or an alkyl radical having 1–4 carbons, provided that at least one of $R_2$ and $R_6$ is hydrogen and provided further that $R_2$–$R_6$ do not contain more than 4 carbons.

The minimum concentration at which these phenols exert this influence is strictly dependent on the concentration of the catalyst with an observed threshold range of 0.3–0.5 times the catalyst concentration. The preferred concentration of phenols is 50–250 mole % of the catalyst concentration. If the mainbody is spiked with the phenol, the preferred concentration of phenols is 0.1–3.0 weight percent of the 2,6-dialkylphenol comprising the main charge of the reaction. The exact increase in catalytic activity depends on the reaction temperature, the total concentration of acidic phenol and the concentration of water at any given moment.

Along with increased catalyst activity, we have observed an increase in diphenoquinone formation in most cases to such an extent that the major product is the diphenoquinone. We believe that the acidic phenols diminish inactivation of the catalyst by water.

Unlike the catalyst described in U.S. Pat. No. 3,631,208, the oxygen activated catalyst system described in this invention can be utilized in the presence of water. Since water is a by-product of the oxidation, this process can be run without having to continuously remove water by distillation which is required in the process described in U.S. Pat. No. 3,631,208.

Product Recovery

The product from the oxidation can be recovered by removing the excess 2,6-dialkylphenol and water byproduct by vacuum distillation at 100°–230° C., preferably at 180° C. to 230° C. At this preferred temperature range, the diphenoquinone product is thermally disproportionated to the desired 3,3′, 5,5′-tetraalkylbiphenol. Operating at this preferred temperature range also results in decomposition of the residual catalyst to insoluble copper oxy halides and TMEDA. In addition, TMEDA from the decomposed catalyst is also removed during the distillation process.

The pure 3,3′, 5,5′-tetraalkylbiphenol can be recovered using known techniques. One example of a suitable isolation procedure is to dissolve the product in a minimum quantity of hot toluene, remove the insoluble copper salts by filtration and recover the product by crystallization. This crude product can be dealkylated by known techniques to produce 4,4′-biphenol (an important starting material for high performance thermoplastics).

The following examples illustrate how our invention may be practiced by those skilled in the art. The invention is not limited to the specific conditions or details set forth in these examples. All examples use the apparatus described in Example 1.

EXAMPLE 1

A 2 liter reaction kettle is charged with 600 ml 2,6-di-tbutylphenol (2,6-DTBP). The kettle lid is fitted with a thermocouple, overhead mechanical stirrer, distillation head/water cooled condenser (in reflux position), sparge tube and septum. The 2,6-DTBP is heated to 97° C. under a nitrogen purge at which point the catalyst is added by removing the septum.

The catalyst is prepared by purging with nitrogen a septum capped flask containing 100 ml 2,6-DTBP and 0.3 g CuCl for 10 min. while the flask contents are heated to 50° C. Purging is continued for 20 min. while the CuCl suspension is vigorously stirred after which time 0.7 g TMEDA is added by syringe, followed by 10 ml air (to impart color to the resulting solution). After a few minutes a dark green homogeneous solution is obtained.

The 2,6-DTBP is heated to 97° C. after the catalyst addition, and the reaction is initiated by terminating the heating and nitrogen purge and commencing oxygen sparging at 2.75 liter/min. the stirring rate is set at about 150 rpm. Over the period of one hour the temperature rises steadily to 117° C. and then drops back to 112° C., average temperature ($T_{av}$): 111° C.

At the end of one hour, sparging is disconntinued and three samples are taken from the reaction mixture for analysis. High performance liquid chromotography of the reaction mixture and authentic standards show that a 46.5% yield of quinone and biphenol is obtained with a ration (%) 3,3′, 5,5′-tetra-t-butyl-4,4′-diphenoquinone (TTBDPQ) : 3,3′, 5,5′-tetra-t-butyl-4,4′-biphenol (TTBBP) of 49:51. Identities of the products are verified by capillary gas chromotography/mass spectrometry.

EXAMPLE 2

The catalyst prepared as described in Example 1 is poured into 700 ml 2,6-DTBP under nitrogen at 79° C. The configuration of the apparatus differs only from Example 1 in that the condenser is set to the condensing position. Oxygen sparging is started at 80° C., and the temperature rises steadily to 105 C.°. Calculated average temperature is 94° C. Analytical results show the ratio TTBDPQ:TTBBP to be 57:43 and a total yield of 41.8%.

EXAMPLE 3

The catalyst prepared according to Example 1 is poured into 600 ml. 2,6-DTBP under nitrogen and heated to 98° C. The condenser is changed to the reflux position, 10 ml of distilled water is added and oxygen sparging initiated. The temperature quickly rises from 98° to 104° C. but then decreases to 72° C. over the period of one hour for an average temperature of 87° C. Product analysis reveals a TTBDPQ:TTBBP ratio of 60:40 with a total yield of 28.9%.

EXAMPLE 4

Using the technique described in Example 1, a catalyst solution using 0.86 g CuBr (instead of CuCl) is prepared. The solution is exposed to air for 5 min. while stirring to give a brown solution. A small amount of residue remains. The catalyst is added to 600 ml 2,6-DTBP at 75° C. and the reaction starts at 98° C. The reaction is run for 1 hour with the condenser in the reflux mode, the temperature rising slowly to 106° C. and then falling to 104° C. ($T_{av}$=104° C.). A product ratio TTBDPQ:TTBBP of 47:53, total yield 33.1% is found.

EXAMPLE 5

The reaction is run as for Example 2 except 0.36 g TMEDA is used in the catalyst, 600 ml 2,6-DTBP for the main charge and 10 ml distilled water is added just prior to oxygen sparging. The reaction temperature starts at 95° C. and slowly declines to 82° C. over a 1 hr. period ($T_{av}$=89° C.). TTBDPQ:TTBBP ratio for the product is 72:28 with a total yield of 37.3%.

EXAMPLE 6

An identical reaction to Example 5 is run except that 1.4 g TMEDA is used in the preparation of the catalyst. While the reaction profile is analogous ($T_{av}=89°$ C.), the TTBDPQ:TTBBP product ratio is 78:22 with a total yield of 30.6% (1 hr.).

EXAMPLE 7

The catalyst is prepared on a larger scale but with the same methodology as described in Example 1 using 3.1 l 2,6-DTBP, 21.3 g CuCl and 49.7 g TMEDA. 100 ml of the catalyst solution is heated to 80° under nitrogen and then pre-activated by sparging with oxygen for 1 minute (2psig, 1 L/min.).

The catalyst is then added to 600 ml 2,6-DTBP at 70° C. (under nitrogen), and the combination is heated to 80° where 10 ml distilled water is added. After three minutes of stirring, oxygen sparging is commenced to initiate the reaction (condenser in reflux position). The temperature of the reaction mixture climbs rapidly from 78° C. to 87° C. and plateaus ($T_{av}=85°$ C.). The ratio of TTBDPQ:TTBBP from product analysis is found to be 84:16 (55.7% total yield).

EXAMPLE 8

A catalyst solution is prepared as follows: 0.3 g $CuCl_2$ and 0.7 g. TMEDA are dissolved in 100 ml methanol (giving a dark blue solution). The catalyst is added to 700 ml 2,6-DTBP at 75° C., and the methanol is distilled from the mixture by gently stirring and heating to 89° C. over the period of one hour with the condenser in the condensing position. After this time, the condenser is set in a reflux position, and oxygen sparging is commenced. The reaction temperature very gradually declines from 93° C. to 89° C. over one hour ($T_{av}=91°$ C.). Analysis shows the TTBDPQ:TTBBP product ratio to be 71:29 with a total yield of 29%.

EXAMPLE 9

The catalyst is prepared and the oxidation run using the method of Example 1, with the exception that 64 mg of phenol (0.01%, total 2,6 charge) is added to the 600 ml charge of 2,6-DTBP. The reaction temperature peaks at 120° C. from 80° C. with a drop to 108° C. ($T_{av}=109°$ C.). Analysis shows the TTBDPQ:TTBBP product ratio to be 65:35 with a total yield of 60%.

EXAMPLE 10

Example 9 is repeated, spiking the 2,6-charge with 0.13 g m-cresol (0.02%). The condenser is in a reflux position. The reaction temperature rises from 80° C. to 101° C. in 55 minutes to give a $T_{av}$ of 95° C. Product analysis reveals a TTBDPQ:TTBBP ratio of 68:32 and a total yield in 55 min. of 44.9%.

EXAMPLES 11-14

These examples are drawn from reactions in which attempts are made to minimize any experimental variations to demonstrate the effect of acidic phenols on the yields of the reaction.

The catalyst solution is prepared by adding 0.3 g. CuCl and 67.3 ml. 2,6-DTBP in a flask. After septum capping, the flask is purged with nitrogen for 15 min. while the flask contents are heated to 50° C. with vigorous stirring. After this time period, 0.7 g TMEDA is added by syringe, and the catalyst solution is stirred for 15 min. at 50° C. Unspiked catalyst solutions are then added to the main 2,6-DTBP body (632.7 ml) (under nitrogen at 98° C.) by quickly pouring into the reaction kettle (the process allows exposure to air equivalent to 5-10 ml air as in Example 1).

After the temperature of the 2,6-DTBP reaches 98° C. again, oxygen sparging at 2.75 l./min is commenced, and agitation is raised from 30 to 150 rpm. After one minute, 5 ml. water is added through the condenser (in the reflux mode). Using a combination of heat and cooling air (with provision for lowering the heating jacket) the average temperature is maintained within 97° C.-100° C. for one hour, after which time three samples are taken from the reaction mixture for analysis by HPLC for 2,6-DTBP, TTBBP and TTBDPQ.

When spiking with acidic phenols is necessary, m-cresol and 2-t-butylphenol are added by syringe to the catalyst solution 15 minutes after TMEDA addition, and are allowed to stir with the catalyst for 10 minutes at 50° C. before transfer to the main 2,6-DTBP charge. The amounts of phenols added (see Table I) brings the concentration to twice that of the CuCl. The 2,6-DTBP catalyst charge contains 0.74 mmol 2-TBP and 25 ppm m-cresol when normal purity 2,6-DTBP is used, and negligible amounts of materials when ultrapure material is selected. The ultrapure 2,6-DTBP is obtained from normal purity 2,6-DTBP by recrystallizing first from 1:1 v/v 1-butanol/methanol and secondly from methanol with a final in vacuo drying period (1 hr, 20mm Hg, 80° C.). Table I shows the total yields obtained (% of theoretical).

TABLE I

Yields of TTBBP/TTBDPQ with Varying Experimental Conditions

| Example | Run Type | Yield, %* | # Runs | % Increase |
|---------|----------|-----------|--------|------------|
| 11 | Normal purity 2,6-DTBP | 17.3, 17.7 av = 17.5 | 2 | — |
| 12 | Ultrapure (99.9%) 2,6-DTBP | 17.3 | 1 | (−)1 |
| 13 | Spiked with 2-TBP | 26.0, 21.3 | 2 | 35 |
| 14 | Spiked with m-cresol | 23.5, 22.4 av = 23.0 | 2 | 31 |

*% of theoretical

The foregoing description relates to preferred embodiments of the present invention, and modifications or alterations may be made without departing from the spirit and scope of the invention as defined in the following claims.

We claim:

1. A process for the manufacture of a mixture of (A) a 3,3', 5,5'-tetralkyl-4,4'- dihydroxybiphenyl having the structural formula I:

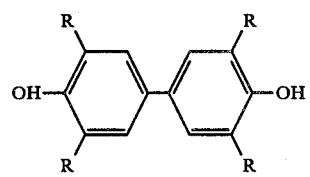

each R being independently an alkyl radical having 3 to 6 carbons; and (B) a 3,3', 5,5'-tetraalky -4,4'-diphenoquinone having the structural formula II:

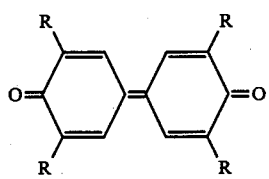

each R being independently an alkyl radical having 3 to 6 carbons; the process comprising the coupling of a 2,6-dialkylphenol in the presence of oxygen, a copper amine salt complex and an acidic phenol, wherein:

(a) the 2,6-dialkylphenol has the structural formula III:

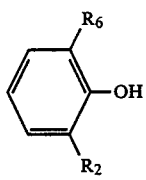

each $R_2$ and $R_6$ being independently an alkyl radical having 3 to 6 carbons;

(b) the acidic phenol is added to either the copper amine salt complex or the 2,6-dialkylphenol; the acidic phenol having the structural formula IV:

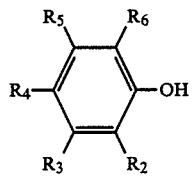

wherein each $R_2$, $R_3$, $R_4$, $R_5$ and $R_6$ is independently hydrogen or an alkyl radical having 1–4 carbons, provided that at least one of $R_2$ and $R_6$ is hydrogen and provided further that $R_2$–$R_6$ do not contain more than 4 carbons;

(c) the copper amine salt complex is prepared by either (1) reacting a copper halide and tetramethylethylenediamine under an inert atmosphere using the 2,6-dialkyphenol as a solvent or (2) air sparging a mixture of a copper halide and tetramethylethylenediamine in a low molecular weight alcohol or halocarbon solvent, wherein the solvent is removed after addition to the 2,6-dialkylphenol/acidic phenol mixture.

2. A process as defined by claim 1 wherein each R in structural formulas I and II is t-butyl.

3. A process as defined by claim 1 wherein each $R_2$ and $R_6$ in structural formula III is t-butyl.

4. A process as defined by claim 1 wherein the copper halide is cuprous chloride, cuprous bromide, cupric chloride or cupric bromide.

5. A process as defined by claim 1 wherein the acidic phenol is 2-t-butyl phenol.

6. A process as defined by claim 1 wherein the acidic phenol is phenol.

7. A process as defined by claim 1 wherein the acidic phenol is m-cresol.

8. A process as defined by claim 1 wherein the acidic phenol is a mixture of m-cresol and 2-t-butyl phenol.

9. A process as defined by claim 1 wherein the 2,6-dialkylphenol described in (c) is 2,6-di-t-butyl phenol.

10. A process as defined by claim 1 wherein the solvent described in (c)(2) is dichloromethane or methanol.

11. A process as defined by claim 1 wherein the molar ratio of copper salt: tetramethylethylenediamine is about 1:0.5–5.

12. A process as defined by claim 1 wherein the total amount of acidic phenol added to the 2,6-dialkylphenol is about 0.2–8 weight percent.

* * * * *

UNITED STATES PATENT AND TRADEMARK OFFICE
CERTIFICATE OF CORRECTION

PATENT NO. : 4,851,589

DATED : July 25, 1989

INVENTOR(S) : Michael D. Cliffton, Stephen J. Carter

It is certified that error appears in the above-identified patent and that said Letters Patent is hereby corrected as shown below:

| Column | Line | | |
|--------|------|---|---|
| 3 | 52 | "1:1.3" should read | --1:1-3-- |
| 3 | 65 | "ration" should read | --ratio-- |
| 6 | 17 | "ration" should read | --ratio-- |

Signed and Sealed this

Twelfth Day of November, 1991

Attest:

HARRY F. MANBECK, JR.

*Attesting Officer*      *Commissioner of Patents and Trademarks*